(12) United States Patent
Kim (10) Patent No.: US 12,232,960 B2
(45) Date of Patent: Feb. 25, 2025

(54) TRICUSPID REGURGITATION SURGICAL INSTRUMENT HAVING POSITION-FIXING TUBE

(71) Applicant: TAU-PNU MEDICAL CO., LTD., Busan (KR)

(72) Inventor: June Hong Kim, Busan (KR)

(73) Assignee: TAU MEDICAL INC., Busan (KR)

( * ) Notice: Subject to any disclaimer, the term of this patent is extended or adjusted under 35 U.S.C. 154(b) by 637 days.

(21) Appl. No.: 17/611,489

(22) PCT Filed: May 18, 2020

(86) PCT No.: PCT/KR2020/006478
§ 371 (c)(1),
(2) Date: Nov. 15, 2021

(87) PCT Pub. No.: WO2020/231237
PCT Pub. Date: Nov. 19, 2020

(65) Prior Publication Data
US 2022/0257368 A1  Aug. 18, 2022

(30) Foreign Application Priority Data
May 16, 2019 (KR) ........................ 10-2019-0057643

(51) Int. Cl.
*A61F 2/24* (2006.01)

(52) U.S. Cl.
CPC ............ *A61F 2/246* (2013.01); *A61F 2/2466* (2013.01); *A61F 2220/0008* (2013.01); *A61F 2250/0059* (2013.01)

(58) Field of Classification Search
CPC ................... A61F 2/246; A61F 2/2466; A61F 2220/0008; A61F 2250/0059; A61B 2017/00243; A61B 17/1285; A61M 29/00
See application file for complete search history.

(56) References Cited

U.S. PATENT DOCUMENTS 7,854,762 B2   12/2010   Speziali et al.
8,486,136 B2    7/2013   Maurer et al.
(Continued)

FOREIGN PATENT DOCUMENTS

| CA | 2206091 A1 * | 6/1995 | .......... A61M 1/3659 |
| KR | 10-1231140 B1 | 2/2013 | |

(Continued)

OTHER PUBLICATIONS

International Search Report issued Feb. 18, 2021 from PCT/USKR2020/006478.
European Search Report issued Apr. 28, 2023 from EP20806883.

*Primary Examiner* — Paul B Prebilic
(74) *Attorney, Agent, or Firm* — Justin H. Kim (57) ABSTRACT

The present disclosure relates to a tricuspid regurgitation surgical instrument having a position-fixing tube that is for temporarily treating tricuspid regurgitation, and more particularly, to a tricuspid regurgitation surgical instrument having a position-fixing tube that is a surgical instrument temporarily inserted into an orifice of the tricuspid valve to check whether right-sided heart failure has occurred, which may occur when tricuspid regurgitation is treated using a permanent method in a patient with tricuspid regurgitation, and that has a position-fixing tube inserted into a coronary sinus so that a blocking part configured to block the orifice of the tricuspid valve penetrates a plane similar to a plane of leaflets of the tricuspid valve and has a penetration angle which allows the blocking part to efficiently block the orifice of the tricuspid valve.

6 Claims, 6 Drawing Sheets

(56) References Cited

U.S. PATENT DOCUMENTS

| | | | |
|---|---|---|---|
| 9,474,605 B2 | 10/2016 | Rowe et al. | |
| 2011/0054597 A1* | 3/2011 | Kim | A61F 2/2463 |
| | | | 623/2.37 |
| 2013/0211513 A1* | 8/2013 | Rourke | A61B 17/0401 |
| | | | 623/2.37 |
| 2013/0325110 A1 | 12/2013 | Khalil | |
| 2017/0119489 A1* | 5/2017 | Kim | A61B 17/0493 |
| 2018/0206989 A1* | 7/2018 | O'Connell | A61F 2/2466 |
| 2019/0350706 A1* | 11/2019 | Kim | A61M 25/01 |

FOREIGN PATENT DOCUMENTS

| | | |
|---|---|---|
| KR | 10-2015-0144568 | 12/2015 |
| KR | 10-2017-0044065 | 4/2017 |
| KR | 10-2019-0020038 | 2/2019 |
| KR | 10-20190012936 | 2/2019 |
| KR | 10-1955291 B1 | 3/2019 |
| KR | 10-1965637 B1 | 4/2019 |

\* cited by examiner

TRICUSPID REGURGITATION SURGICAL INSTRUMENT HAVING POSITION-FIXING TUBE

TECHNICAL FIELD

The present disclosure relates to a tricuspid regurgitation surgical instrument having a position-fixing tube that is for temporarily treating tricuspid regurgitation, and more particularly, to a tricuspid regurgitation surgical instrument having a position-fixing tube that is a surgical instrument temporarily inserted into an orifice of the tricuspid valve to check whether right-sided heart failure has occurred, which may occur when tricuspid regurgitation is treated using a permanent method in a patient with tricuspid regurgitation, and that has a position-fixing tube inserted into the coronary sinus so that a blocking part configured to block the orifice of the tricuspid valve penetrates a plane similar to a plane of leaflets of the tricuspid valve and has a penetration angle which allows the blocking part to efficiently block the orifice of the tricuspid valve.

BACKGROUND ART

Tricuspid regurgitation is also referred to as tricuspid valve insufficiency. Tricuspid regurgitation refers to a symptom in which, due to a lesion of the tricuspid valve, the tricuspid valve does not completely close when it should be closed, causing an orifice to be formed, and during contraction of the right ventricle, some of the blood that has to flow from the right ventricle to the pulmonary artery flows back into the right atrium through the orifice.

Conventional methods of treating tricuspid regurgitation include a method in which the patient's chest is opened and an incision is made in the heart to make a surgical correction and a method in which, as proposed in U.S. Pat. No. 8,486,136 B2, U.S. Pat. No. 7,854,762 B2, and U.S. Pat. No. 9,474,605 B2, a tricuspid regurgitation surgical instrument is permanently inserted into the patient's body to treat tricuspid regurgitation. However, when tricuspid regurgitation is treated using the above surgical method or permanent method, there are problems in that right ventricular volume overload occurs due to a sudden increase in blood flow from the right ventricle to the pulmonary artery, and right-sided heart failure occurs.

Thus, in order to address the above problems, the inventor of the present disclosure has developed a device capable of temporarily blocking an orifice of the tricuspid valve to check whether right-sided heart failure has occurred, has published the device in a patent application publication, and has been granted a patent (Korean Patent Registration No. 10-1965637 (Title of Invention: A device for the treatment of tricuspid regurgitation in the pulmonary artery).

The device for treatment of tricuspid regurgitation in the pulmonary artery that is published in the above patent (Korean Patent Registration No. 10-1965637) includes a blocking part which is configured to block an orifice of the tricuspid valve, an insertion tube which has a guide wire guiding lumen formed therein to be movable along a guide wire, and a sheath tube which has a lumen formed to insert the blocking part and the insertion tube thereinto.

The insertion tube is inserted into the inferior vena cava, tricuspid valve, and pulmonary artery along the guide wire, the blocking part penetrates the orifice of the tricuspid valve to temporarily block the orifice and determine whether right-sided heart failure has occurred, and then the device is removed from the body.

However, since a distance between the inferior vena cava (IVC) and tricuspid valve (TV) varies for each patient, in some cases, the orifice of the TV is not accurately blocked during a surgical procedure using the device.

For example, in the case of a patient with severe tricuspid regurgitation in which a distance between the IVC and TV is long, in some cases, a TV penetration angle of the blocking part coupled to the insertion tube moving to the IVC, TV, and pulmonary artery is changed, and thus the blocking part is not able to accurately block the orifice of the TV. Also, in some cases, as the insertion tube is rotated to the left or right, the blocking part is tilted toward one side in the left-right direction and is not able to form a plane similar to a plane of leaflets of the TV, thus not being able to accurately block the orifice.

Therefore, there is a need for a tricuspid regurgitation surgical instrument that allows efficient treatment also for tricuspid regurgitation patients with a long IVC-TV distance and that is not rotated or moved after being placed, thus not causing movement of a blocking part configured to block an orifice of the TV.

DISCLOSURE

Technical Problem

The present disclosure is directed to providing a tricuspid regurgitation surgical instrument having a position-fixing tube that forms a penetration angle at which a blocking part efficiently penetrates an orifice of the tricuspid valve so that the blocking part accurately blocks the orifice of the tricuspid valve even for patients in which a distance between the inferior vena cava and tricuspid valve is long.

The present disclosure is also directed to providing a tricuspid regurgitation surgical instrument having a position-fixing tube that allows a blocking part to be easily placed on a plane similar to a plane of leaflets of the tricuspid valve and, after the blocking part is placed, prevents the blocking part from moving toward one side in the left-right direction, thus efficiently blocking an orifice of the tricuspid valve.

The objectives of the present disclosure are not limited to those mentioned above, and other unmentioned objectives should be clearly understood by those of ordinary skill in the art from the description below.

Technical Solution

The present disclosure provides a tricuspid regurgitation surgical instrument having a position-fixing tube, the tricuspid regurgitation surgical instrument including: an insertion tube which has a lumen, into which a first guide wire is inserted, formed therein to be movable from the inferior vena cava or superior vena cava to the pulmonary artery along the first guide wire; a membrane-type blocking part which is coupled to one outer side surface of the insertion tube, obliquely penetrates an orifice formed due to incomplete closing of the tricuspid valve, and is made of a material which is suitable for the human body and is flexible but does not tear easily; and a position-fixing tube which is coupled to the other outer side surface of the insertion tube and has a lumen, into which a second guide wire is inserted, formed therein, a coupling part disposed at a proximal part and coupled to the insertion tube to a predetermined length, and a separated part disposed at a distal part and separated from the insertion tube, wherein the separated part formed at the distal part of the position-fixing tube is inserted into the coronary sinus to prevent rotation or vertical movement of the insertion tube and the blocking part.

The position-fixing tube and the blocking part may be disposed at opposite directions from each other with respect to the insertion tube and may be disposed to be coplanar.

Here, the tricuspid regurgitation surgical instrument may further include a coupling tube which has one side into which the insertion tube and the proximal part of the position-fixing tube are inserted so as to come into close contact with the insertion tube and the position-fixing tube and has the other side disposed outside the body and fixed outside the body to prevent rotation or movement of the insertion tube and the position-fixing tube during a surgical procedure.

The insertion tube may have a curved part curved at a predetermined angle formed therein to allow the blocking part to be more accurately inserted into the orifice.

The blocking part may include a support wire which has both ends coupled to the insertion tube and a blocking membrane which has one side fixed to the insertion tube and is supported by the support wire.

According to another embodiment, the blocking part may include a ring-shaped wire which is installed to penetrate the insertion tube and has a central axis formed obliquely to the insertion tube and a blocking membrane which is configured to connect the insertion tube and the ring-shaped wire.

Advantageous Effects

A tricuspid regurgitation surgical instrument having a position-fixing tube according to the present disclosure includes a position-fixing tube inserted into the coronary sinus to form a tricuspid valve penetration angle at which a blocking part effectively blocks an orifice of the tricuspid valve regardless of a distance between the inferior vena cava and tricuspid valve. By maintaining the penetration angle to be constant at all times, tricuspid regurgitation can be treated more effectively and conveniently.

Also, the blocking part and the position-fixing tube are formed at opposite directions from each other with respect to an insertion tube such that, when the position-fixing tube is inserted into the coronary sinus, the blocking part naturally penetrates the orifice of the tricuspid valve on a plane similar to a plane of leaflets of the tricuspid valve, and the blocking part is not tilted toward one side in the left-right direction. Thus, the orifice of the tricuspid valve can be effectively blocked.

In addition, the position-fixing tube and the insertion tube have proximal parts coupled to each other and distal parts separated from each other, and first and second guide wires inserted into the body in advance is inserted into each of the position-fixing tube and the insertion tube so that the position-fixing tube and the insertion tube easily move into the body along the first and second guide wires. In this way, the surgical procedure is facilitated.

DESCRIPTION OF REFERENCE NUMERALS

1: guide wire
10: blocking part
12: blocking membrane
14: support wire
16: ring-shaped wire
20: insertion tube
22: insertion tube lumen
24: curved part
30: position-fixing tube
32: coupling part
34: separated part
36: position-fixing tube lumen
40: coupling tube
42: coupling tube lumen

MODES OF THE INVENTION

Hereinafter, exemplary embodiments of the present disclosure will be described in detail with reference to the accompanying drawings.

Figure 1:
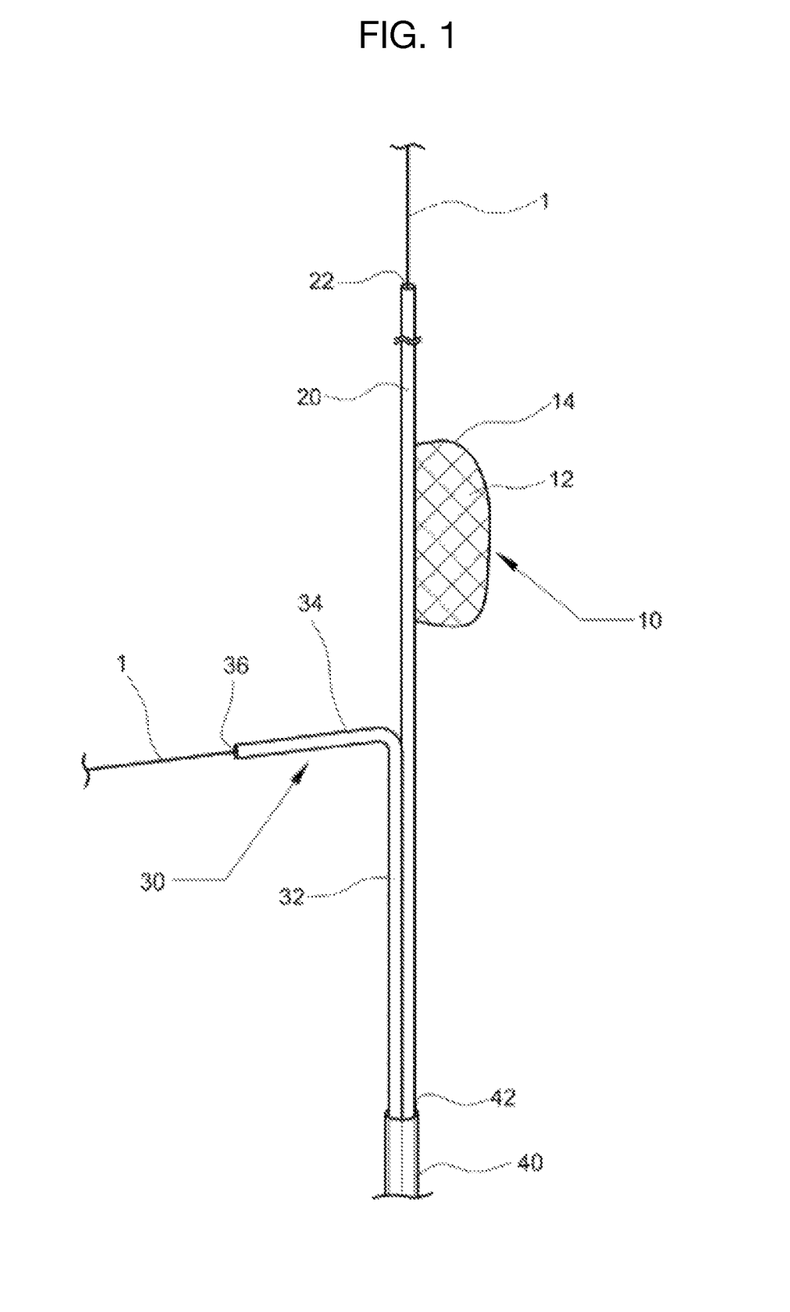
FIG. 1 is a perspective view of a tricuspid regurgitation surgical instrument having a position-fixing tube according to an exemplary embodiment of the present disclosure.

FIG. 1 is a perspective view of a tricuspid regurgitation surgical instrument having a position-fixing tube according to an exemplary embodiment of the present disclosure.

Referring to FIG. 1, the tricuspid regurgitation surgical instrument having a position-fixing tube according to an exemplary embodiment of the present disclosure includes a blocking part 10, an insertion tube 20, and a position-fixing tube 30.

The blocking part 10 is coupled to an outer side surface of the insertion tube 20 and includes a blocking membrane 12 and a support wire 14. The support wire 14 has both ends fixed to the insertion tube 20, and the blocking membrane 12 connects the insertion tube 20 and the support wire 14. Of course, in some cases, neither side or only one side of the support wire 14 may be fixed to the insertion tube 20.

For the blocking membrane 12, a material which is suitable for the human body and is flexible but does not tear easily is used. For example, medical grade polyurethane, polyolefin, silicone, e-polytetrafluoroethylene (e-PTFE), polytetrafluoroethylene (PTFE), etc. may be used.

The support wire 14 is for holding the shape of the blocking membrane 12, and for the support wire 14, a wire made of a synthetic resin such as nylon or a wire made of metal (stainless steel, a metal coated with nylon, etc.) may be used. The support wire 14 may be a single wire or may be a type of wire made by twisting a plurality of thin wires.

Also, the blocking membrane 12 may be doubly formed, and the support wire 14 may be configured to be inserted into the blocking membrane 12.

Figure 2:
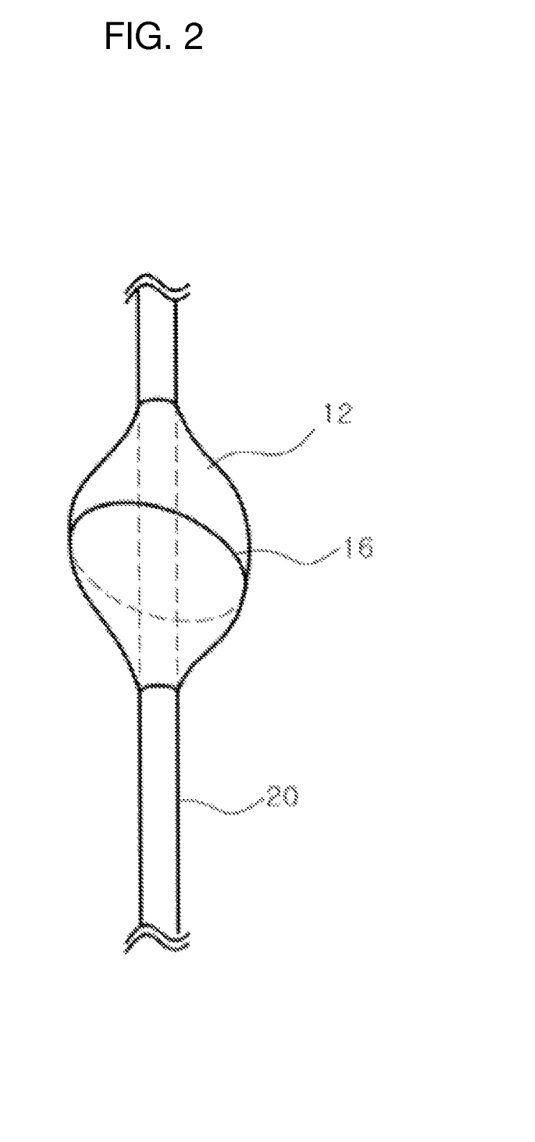
FIG. 2 is an enlarged perspective view of a blocking part according to another embodiment of the present disclosure.

FIG. 2 illustrates a blocking part according to another embodiment of the present disclosure. Referring to FIG. 2, a blocking part 10 according to another embodiment of the present disclosure includes a ring-shaped wire 16 which is installed to penetrate the insertion tube 20 and has a central axis formed obliquely to the insertion tube 20 and a blocking membrane 12 which is configured to connect the ring-shaped wire 16 and the insertion tube 20.

Due to being tilted at a predetermined angle and obliquely installed at the insertion tube 20, the ring-shaped wire 16 is disposed to be parallel to the tricuspid valve. Therefore, the ring-shaped wire 16 may effectively block an orifice of the tricuspid valve.

Referring back to FIG. 1, the insertion tube 20 has an insertion tube lumen 22, into which a first guide wire 1 is inserted, formed therein and is made of a material such as rubber or flexible plastic such that the insertion tube 20 has high flexibility and restorability that allow the insertion tube 20 to move according to the beating of the heart.

The insertion tube 20 is inserted into the inferior vena cava, tricuspid valve, and pulmonary artery along the first guide wire 1 so that the blocking part 10 penetrates the orifice of the tricuspid valve to block the orifice of the tricuspid valve. The insertion tube 20 according to an exemplary embodiment of the present disclosure is formed long so that one end is disposed in the pulmonary artery and the other end is disposed outside the body.

Here, the guide wire 1 includes two guide wires 1, one of which is inserted into the body in advance along the inferior vena cava or superior vena cava, the tricuspid valve, and the pulmonary artery and inserted into the insertion tube lumen 22 to assist in movement of the insertion tube 20 inside the body, and the other one of which is inserted into the body in advance along the inferior vena cava or superior vena cava and the coronary sinus and inserted into the position-fixing tube 30 to assist in movement of the position-fixing tube 30 inside the body.

For the guide wire 1, a wire made of a synthetic resin such as nylon or a wire made of metal (stainless steel, a metal coated with nylon, etc.) may be used. The guide wire 1 may be a single wire or may be a type of wire made by twisting a plurality of thin wires.

The position-fixing tube 30 is coupled to an outer side surface of the insertion tube 20 and has a position-fixing tube lumen 36, into which the second guide wire 1 is inserted, formed therein.

The position-fixing tube 30 includes a coupling part 32 which is disposed at a proximal part and coupled to the insertion tube 20 to a predetermined length and a separated part 34 which is disposed at a distal part and separated from the insertion tube 20.

The position-fixing tube 30 may be made of a material such as rubber or flexible plastic. The material used has high flexibility and restorability and thus allows the position-fixing tube 30 to move according to the beating of the heart.

Here, the position-fixing tube 30 may be coupled to the insertion tube 20 in a direction different from a direction in which the blocking part 10 is coupled to the insertion tube 20. Preferably, the position-fixing tube 30 and the blocking part 10 may be coupled to the insertion tube 20 in directions 180° opposite each other and may be disposed to be coplanar.

The position-fixing tube 30 is moved inside the body along the second guide wire 1 which is inserted in advance from the inferior vena cava or superior vena cava to the coronary sinus, and the separated part 34 of the position-fixing tube 30 is inserted into the coronary sinus.

The coronary sinus is formed at a position adjacent to leaflets of the tricuspid valve, and a distance between the coronary sinus and tricuspid valve is similar in all patients. That is, unlike a distance between the inferior vena cava and tricuspid valve, the distance between the coronary sinus and tricuspid valve does not vary greatly from patient to patient and is similar in all patients.

Therefore, due to the separated part 34 of the position-fixing tube 30 being inserted into the coronary sinus, a penetration angle at which the blocking part 10 penetrates the orifice of the tricuspid valve may be constant for all patients during the surgical procedure.

Also, due to the separated part 34 of the position-fixing tube 30 being inserted into the coronary sinus, the insertion tube 20 has a path of being moved from the inferior vena cava or superior vena cava to the inlet of the coronary sinus, the tricuspid valve, and the pulmonary artery and, accordingly, allows a central portion of the blocking part 10 to be disposed in the orifice of the tricuspid valve, thus efficiently blocking the orifice.

Also, due to the separated part 34 being inserted into the coronary sinus, rotation or vertical movement of the insertion tube 20 and the blocking part 10 may be prevented.

Here, since the position-fixing tube 30 and the blocking part 10 are coupled to the insertion tube 20 in directions 180° opposite each other and are disposed to be coplanar, when the separated part 34 of the position-fixing tube 30 is inserted into the coronary sinus, the blocking membrane 12 of the blocking part 10 may, without being tilted toward one side in the left-right direction, maintain a plane similar to a plane of leaflets of the tricuspid valve and penetrate the orifice of the tricuspid valve to efficiently block the orifice.

Due to having the separated part 34 formed at the distal part and inserted into the coronary sinus, the position-fixing tube 30 according to an exemplary embodiment of the present disclosure is formed long so that one end is disposed in the coronary sinus and the other end is disposed outside the body.

The tricuspid regurgitation surgical instrument to which the position-fixing tube according to the present disclosure is coupled further includes a coupling tube 40. The coupling tube 40 has a coupling tube lumen 42 formed therein, and the insertion tube 20 and the proximal part of the position-fixing tube 30 are inserted into the coupling tube lumen 42 so that the coupling tube 40 comes into close contact with the insertion tube 20 and the position-fixing tube 30 and fixes the insertion tube 20 and the position-fixing tube 30.

The coupling tube 40 may be made of a material such as rubber or flexible plastic. The material used has high flexibility and restorability and thus allows the coupling tube 40 to move according to the beating of the heart. The coupling tube 40 is formed to have a diameter larger than a diameter of each of the insertion tube 20 and the position-fixing tube 30 so that the insertion tube 20 and the position-fixing tube 30 may be inserted into the coupling tube 40.

The coupling tube 40 has one side disposed inside the body and the other side disposed outside the body. By temporarily fixing the other side of the coupling tube 40, the insertion tube 20 and the position-fixing tube 30 are prevented from moving or rotating leftward or rightward inside the body, and the tricuspid regurgitation surgical instrument having a position-fixing tube according to the present disclosure is able to be temporarily inserted into the body and fixed or removed therefrom.

Figure 3:
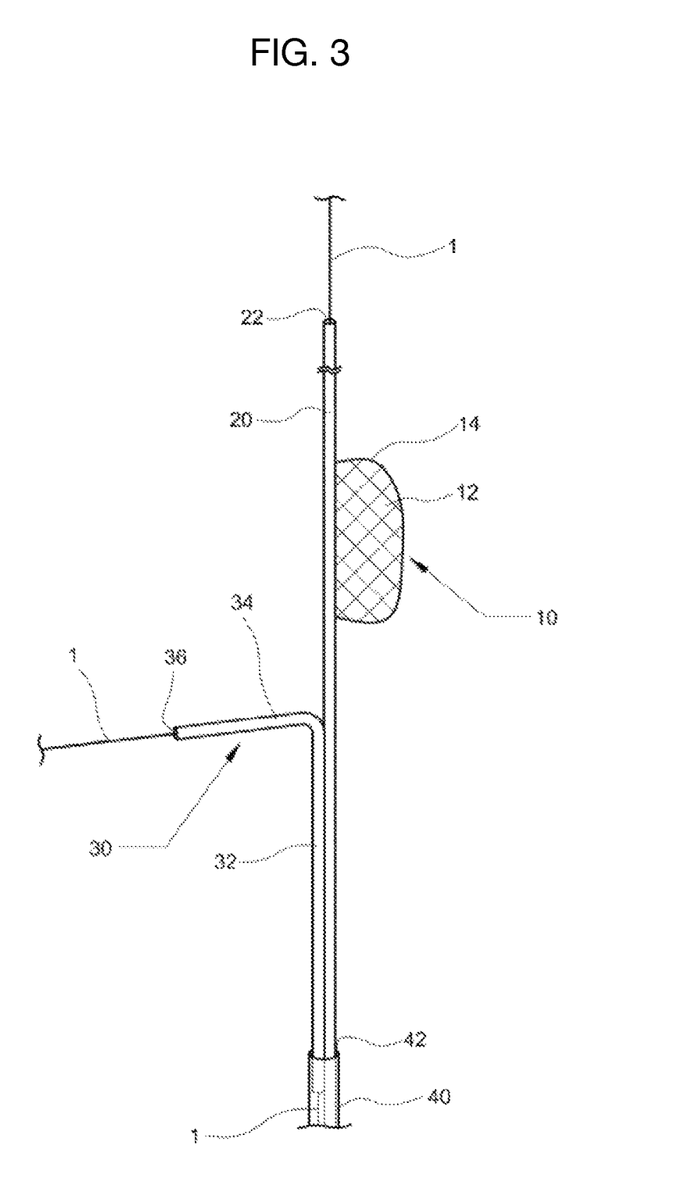
FIG. 3 is a perspective view of a tricuspid regurgitation surgical instrument having a position-fixing tube according to another exemplary embodiment of the present disclosure.

FIG. 3 is a perspective view of a tricuspid regurgitation surgical instrument having a position-fixing tube according to another exemplary embodiment of the present disclosure.

Referring to FIG. 3, the tricuspid regurgitation surgical instrument having a position-fixing tube according to another exemplary embodiment of the present disclosure includes a position-fixing tube 30 having a shorter length than the position-fixing tube 30 illustrated in FIG. 1.

More specifically, the position-fixing tube 30 according to another exemplary embodiment of the present disclosure includes a coupling part 32, a separated part 34, and a position-fixing tube lumen 36. During the surgical procedure, the separated part 34 at a distal part is inserted into the coronary sinus such that one end of the position-fixing tube 30 is placed in the coronary sinus, and the coupling part 32 at a proximal part is coupled to the insertion tube 20 at an outer side surface of the insertion tube 20 such that the other side of the position-fixing tube 30 is placed inside the body.

Therefore, the position-fixing tube 30 according to another embodiment of the present disclosure has a characteristic of being formed to have a shorter length than the position-fixing tube 30 illustrated in FIG. 1, and all the other configurations are the same as those described above with reference to FIG. 1.

Figure 4:
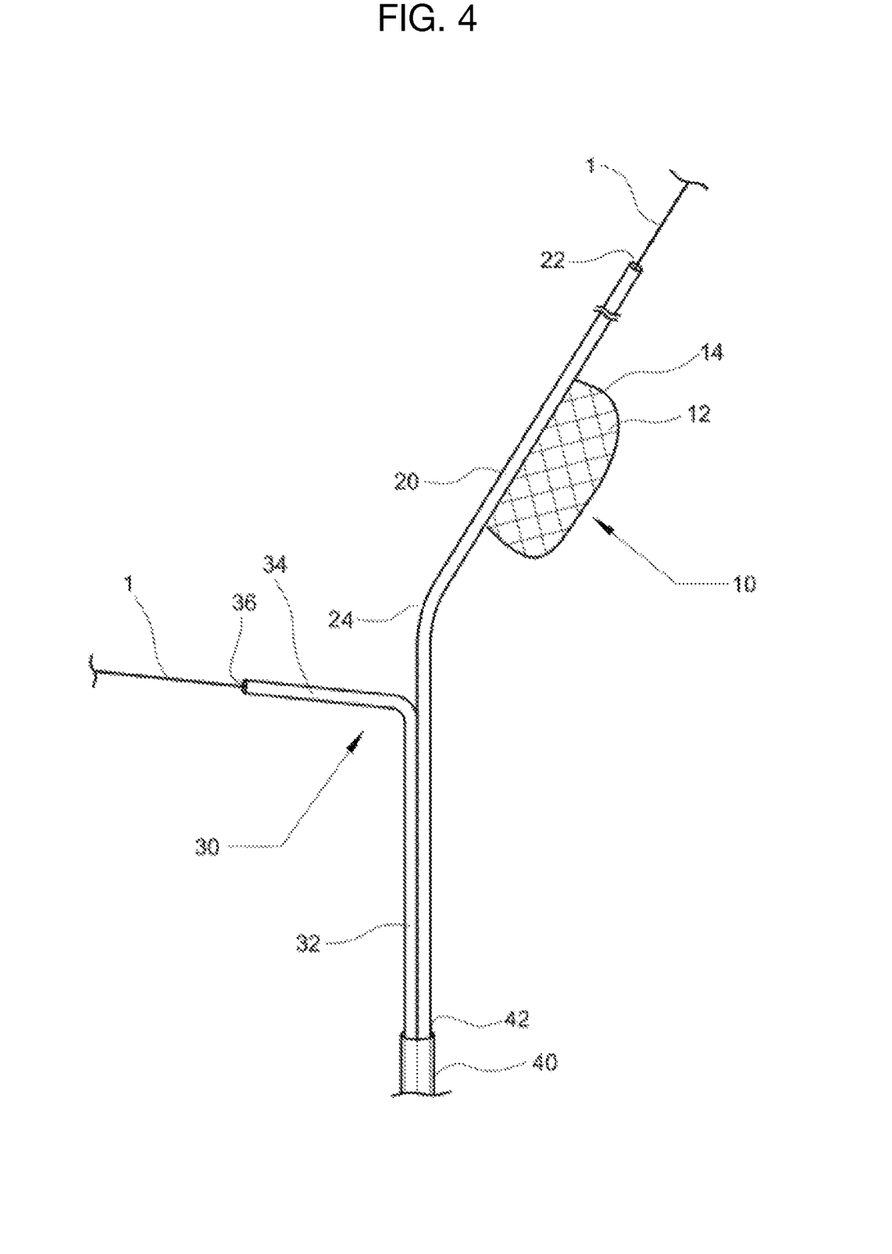
FIG. 4 is a perspective view of a tricuspid regurgitation surgical instrument having a position-fixing tube according to still another exemplary embodiment of the present disclosure.

FIG. 4 is a perspective view of a tricuspid regurgitation surgical instrument having a position-fixing tube according to still another exemplary embodiment of the present disclosure.

In the tricuspid regurgitation surgical instrument having a position-fixing tube according to still another exemplary embodiment of the present disclosure, an insertion tube 20 includes a curved part 24.

The curved part 24 of the insertion tube 20 is curved at a predetermined angle to form a tricuspid valve penetration angle that allows a blocking part 10 to effectively block an orifice of the tricuspid valve. The penetration angle is maintained to be constant at all times regardless of the length between the inferior vena cava and tricuspid valve.

A single curved part 24 is illustrated in FIG. 4, but of course, a plurality of curved parts 24 may be formed. Configurations other than the insertion tube 20 are the same as those described above with reference to FIG. 1.

Figure 5:
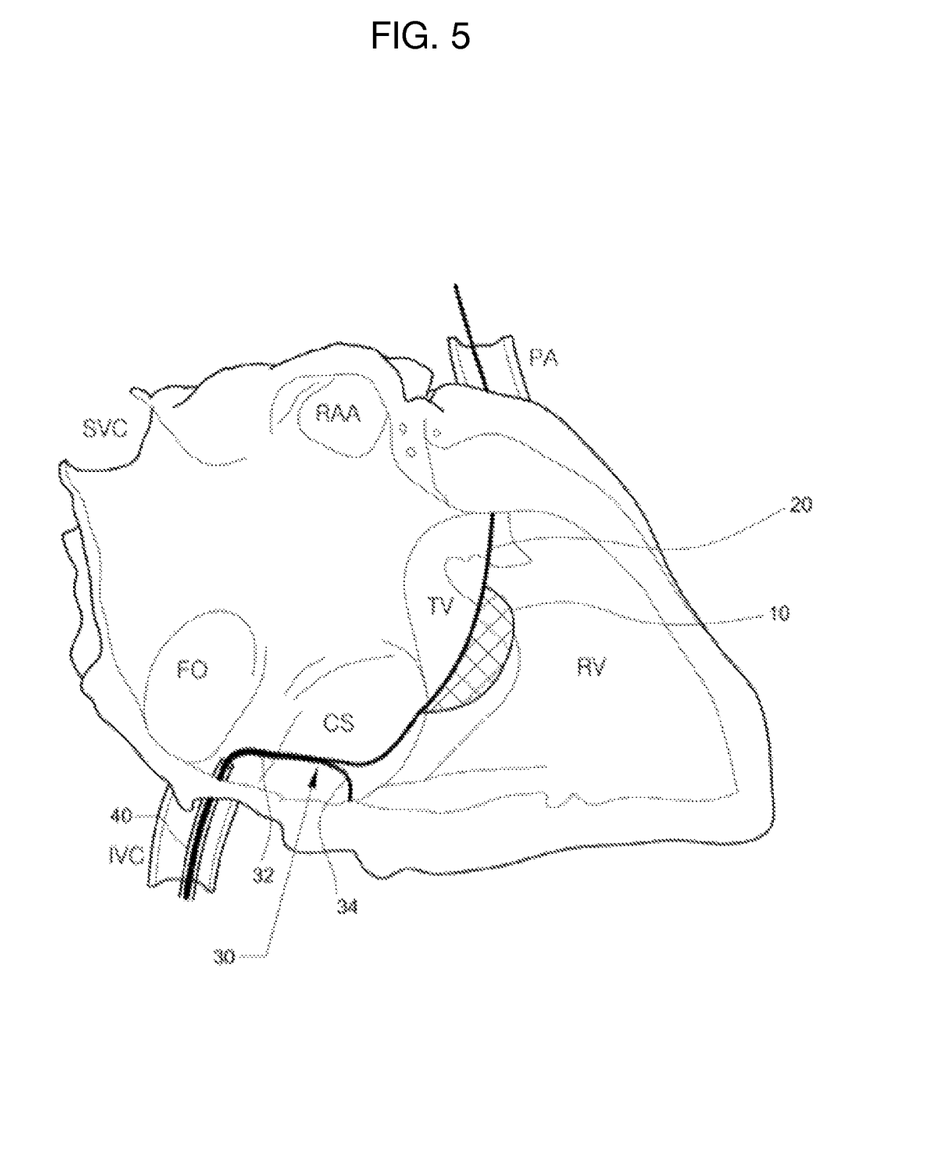
FIG. 5 is a cross-sectional view illustrating a state in which a tricuspid regurgitation surgical instrument having a position-fixing tube according to an exemplary embodiment is inserted into the inferior vena cava, tricuspid valve, and pulmonary artery.
Figure 6:
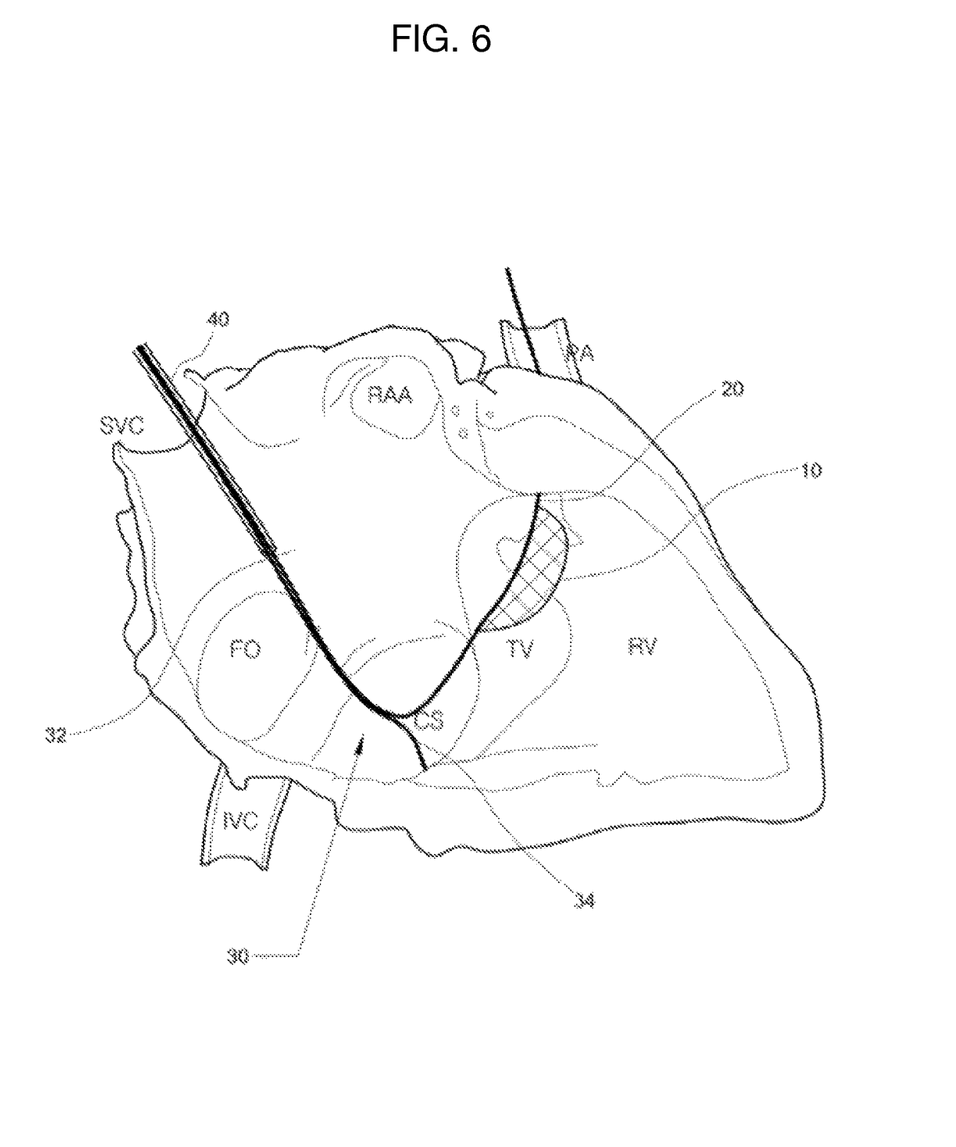
FIG. 6 is a cross-sectional view illustrating a state in which the tricuspid regurgitation surgical instrument having a position-fixing tube according to an exemplary embodiment is inserted into the superior vena cava, tricuspid valve, and pulmonary artery.

FIG. 5 is a cross-sectional view illustrating a state in which a tricuspid regurgitation surgical instrument having a position-fixing tube according to an exemplary embodiment of the present disclosure is inserted into the inferior vena cava, tricuspid valve, and pulmonary artery, and FIG. 6 is a cross-sectional view illustrating a state in which the tricuspid regurgitation surgical instrument having a position-fixing tube according to an exemplary embodiment is inserted into the superior vena cava, tricuspid valve, and pulmonary artery.

A process of inserting the tricuspid regurgitation surgical instrument having a position-fixing tube according to an exemplary embodiment of the present disclosure into the body will be described with reference to FIGS. 5 and 6.

First, as in FIG. 5, for the tricuspid regurgitation surgical instrument having a position-fixing tube to be inserted into the inferior vena cava, tricuspid valve, and pulmonary artery, two guide wires 1 are inserted into the body. One guide wire 1 is inserted into a tricuspid valve TV and a pulmonary artery PA from an inferior vena cava IVC, and the other guide wire 1 is inserted into a coronary sinus CS from the inferior vena cava IVC.

The insertion tube 20 and the position-fixing tube 30 are moved into the body along the two guide wires 1 inserted into the body beforehand. The insertion tube 20 is moved into the body along the first guide wire 1 inserted into the inferior vena cava, tricuspid valve, and pulmonary artery, and the position-fixing tube 30 is moved into the body along the second guide wire 1 inserted into the inferior vena cava and coronary sinus.

As in FIG. 6, for the tricuspid regurgitation surgical instrument having a position-fixing tube to be inserted into the superior vena cava, tricuspid valve, and pulmonary artery, first, two guide wires 1 are inserted into the body. One guide wire 1 is inserted into the tricuspid valve TV and the pulmonary artery PA from a superior vena cava SVC, and the other guide wire 1 is inserted into the coronary sinus CS from the superior vena cava SVC.

The insertion tube 20 and the position-fixing tube 30 are inserted along the two guide wires 1 inserted into the body beforehand. The insertion tube 20 is inserted along the first guide wire 1 inserted into the superior vena cava, tricuspid valve, and pulmonary artery, and the position-fixing tube 30 is inserted along the second guide wire 1 inserted into the superior vena cava and coronary sinus.

Subsequent processes are the same for FIGS. 5 and 6. The blocking part 10 is coupled to an outer side surface of the insertion tube 20 and is moved into the body along the insertion tube 20 to penetrate an orifice of the tricuspid valve.

The blocking part 10 is coupled to an outer side surface of the insertion tube 20 and is moved into the body along the insertion tube 20 to penetrate an orifice of the tricuspid valve.

Here, the insertion tube 20 and the position-fixing tube 30 are made of a flexible material that is bendable along a path in which the guide wire 1 is inserted inside the body.

Also, when making the tricuspid regurgitation surgical instrument having the second guide wire 1 or the position-fixing tube enter the body, a sheath tube (not illustrated) may be further included so that the tricuspid regurgitation surgical instrument moves into the body while being inserted into the sheath tube (not illustrated), and the sheath tube (not illustrated) may be removed from the body after the movement is complete.

The position-fixing tube 30 includes the coupling part 32 and the separated part 34. The coupling part 32 is coupled to the insertion tube 20, and the separated part 34 is inserted into the coronary sinus to form a penetration angle that allows the blocking part 10 to effectively block the orifice of the tricuspid valve.

Also, since the position-fixing tube 30 and the blocking part 10 are coupled to the insertion tube 20 in directions opposite from each other, when the position-fixing tube 30 is inserted into the coronary sinus, the blocking membrane 12 of the blocking part 10 may, without being tilted toward one side in the left-right direction, maintain a plane similar to a plane of leaflets of the tricuspid valve and penetrate the orifice of the tricuspid valve.

Once the blocking part 10 has penetrated the orifice of the tricuspid valve, the guide wire 1 is removed from the body, and the coupling tube 40 is inserted into the body. The insertion tube 20 and the position-fixing tube 30 are inserted into the coupling tube lumen 42 formed inside the coupling tube 40 such that the coupling tube 40 comes into close contact with the insertion tube 20 and the position-fixing tube 30, and an end of the coupling tube 40 is placed outside the body and fixed.

Therefore, the insertion tube 20 and the position-fixing tube 30 are fixed so as not to move or rotate after being inserted into the body, and thus the orifice of the tricuspid valve may be stably blocked.

An operator may easily and conveniently insert the tricuspid regurgitation surgical instrument having a position-fixing tube according to the present disclosure into the body for a predetermined amount of time to check whether right-sided heart failure has occurred.

Also, since the position-fixing tube is inserted into the coronary sinus, even for a patient with a long distance between the inferior vena cava and tricuspid valve, it is possible to form a penetration angle that allows the blocking part to efficiently block the orifice. Since the blocking part maintains a plane similar to a plane of leaflets of the tricuspid valve and penetrates the orifice of the tricuspid valve without being tilted toward one side in the left-right direction, the orifice formed due to incomplete closing of the tricuspid valve may be efficiently blocked. In this way, tricuspid regurgitation may be treated.

The embodiments of the present disclosure have been described above with reference to the accompanying drawings, but those of ordinary skill in the art to which the present disclosure pertains should understand that the present disclosure may be embodied in other specific forms without changing the technical idea or essential features of the present disclosure. Therefore, the embodiments described above should be understood as being illustrative, instead of limiting, in all aspects.

The invention claimed is:

1. A tricuspid regurgitation surgical instrument having a position-fixing tube, the tricuspid regurgitation surgical instrument comprising:
    an insertion tube which has a lumen, into which a first guide wire is inserted, formed therein to be movable from an inferior vena cava or superior vena cava to a pulmonary artery along the first guide wire;
    a blocking part which is coupled to one outer side surface of the insertion tube, structured to obliquely pass through an orifice formed due to incomplete closing of the tricuspid valve, and is made of a material which is suitable for the human body and is flexible but does not tear easily; and
    a position-fixing tube which is coupled to another outer side surface of the insertion tube and has a lumen, into which a second guide wire is inserted, formed therein, a coupling part disposed at a proximal part and coupled to the insertion tube to a predetermined length, and a separated part disposed at a distal part and separated from the insertion tube,
    wherein the separated part formed at the distal part of the position-fixing tube is structured to be inserted into a coronary sinus to prevent rotation or vertical movement of the insertion tube and the blocking part;
    wherein the blocking part includes a ring-shaped wire which is installed to penetrate the insertion tube and has a central axis formed obliquely to the insertion tube and a blocking membrane which is configured to connect the insertion tube and the ring-shaped wire.

2. The tricuspid regurgitation surgical instrument of claim 1, wherein the position-fixing tube and the blocking part are disposed at opposite directions from each other with respect to the insertion tube.

3. The tricuspid regurgitation surgical instrument of claim 1, wherein the position-fixing tube and the blocking part are disposed to be coplanar.

4. The tricuspid regurgitation surgical instrument of claim 1, further comprising a coupling tube which has one side into which the insertion tube and the proximal part of the position-fixing tube are inserted so as to come into close contact with the insertion tube and the position-fixing tube and has the other side configured to be disposed outside the body and fixed outside the body to prevent rotation or movement of the insertion tube and the position-fixing tube during a surgical procedure.

5. The tricuspid regurgitation surgical instrument of claim 1, wherein the insertion tube has a curved part curved at a predetermined angle formed therein to allow the blocking part to be more accurately inserted into the orifice.

6. The tricuspid regurgitation surgical instrument of claim 1, wherein the blocking part includes a support wire which has both ends coupled to the insertion tube and a blocking membrane which has one side fixed to the insertion tube and is supported by the support wire.

* * * * *